United States Patent [19]

Laure

[11] 4,040,130

[45] Aug. 9, 1977

[54] WRIST JOINT PROSTHESIS

[75] Inventor: George R. Laure, Kalamazoo, Mich.

[73] Assignee: Laure Prosthetics, Inc., Portage, Mich.

[21] Appl. No.: 731,795

[22] Filed: Oct. 12, 1976

[51] Int. Cl.² ............................................. A61F 1/24
[52] U.S. Cl. .................................. 3/1.91; 128/92 C
[58] Field of Search ............................ 3/1, 1.9–1.913, 3/12.4; 128/92 C, 92 CA

[56] References Cited

U.S. PATENT DOCUMENTS

| 3,506,982 | 4/1970 | Steffee | 3/1.91 |
|---|---|---|---|
| 3,837,008 | 9/1974 | Bahler | 3/1.91 |
| 3,842,442 | 10/1974 | Kolbel | 3/1.91 |
| 3,909,853 | 10/1975 | Lennox | 3/1.91 |
| 3,916,451 | 11/1975 | Buechel et al. | 3/1.91 |
| 4,003,096 | 1/1977 | Frey | 3/1.91 |

FOREIGN PATENT DOCUMENTS

| 2,309,432 | 11/1973 | Germany | 3/1.91 |

*Primary Examiner*—Ronald L. Frinks
*Attorney, Agent, or Firm*—Blanchard, Flynn, Thiel, Boutell & Tanis

[57] ABSTRACT

Wrist joint prosthesis. As a replacement for the joint in a human wrist, there is provided a prosthesis permitting both vertical motion, sidewise motion and rotary motion but preventing twisting motion around an axis projecting from and parallel with the lower forearm. For this purpose, there is provided a metal socket fitted with a prong receivable into a bone of the forearm. A plastic cup made of material self-lubricating with respect to such metal socket is fitted within said socket, snappable thereinto to resist but not prevent withdrawal therefrom and having a rectangular projection-and-slot relationship with said metal socket to permit relative motion with respect thereto in only a single plane. A metal ball is receivable into the recess of said plastic cup, snappable therewith to resist but not prevent withdrawal therefrom and has a rectangular projection-and-slot relationship with the inside of said plastic cup to permit relative movement with respect thereto in only a single plane, said plane being substantially perpendicular to said first-named plane. Suitable projections are provided on said ball for reception into the bones of selected fingers, normally the index and middle finger. Placement of said prosthesis in one position or a mirror image thereof will render said prosthesis without other change adaptable for use with one hand or the other hand as desired.

9 Claims, 8 Drawing Figures

FIG.1

WRIST JOINT PROSTHESIS

FIELD OF THE INVENTION

The invention relates to endoprosthetic joints, and more particularly to an endoprostheses for a wrist joint which will be durable and capable of withstanding strenuous usage; which may be solidly implanted into the body of a subject human and resist displacement, twisting or migration with respect to the surrounding bone; which will closely approximate the motion of a healthy, natural joint; and which will be relatively easy to insert and thereafter cause a minimum of pain, discomfort or restriction of activity in the subject.

BACKGROUND OF THE INVENTION

The subject of endoprosthetic joints has received a great deal of attention over the past several years and has particularly received much attention in recent years due in part to the availability of improved materials inert to human or animal bodies and to improved techniques for manipulating same. However, in spite of such intensive study, the endoprosthetic joints previously available, while in many cases satisfactory to a limited degree, are far from fully satisfactory and intensive work is continuing for the further improvement of such prostheses.

In one particular area, namely that of wrist joints, previous efforts have proven highly frustrating due to the complex nature of wrist joint action and particularly due to the desirability of having substantially universal motion between the hand and the arm but preventing twisting motion between the hand and the arm around an axis projecting from the arm as a substantial continuation of the central axis thereof. In addition, it is essential to provide a joint which can be assembled quickly and easily during the implanting procedure but which after assembly will provide a strong joint capable of withstanding the heavy pressures to which a wrist is subjected during normal use thereof. Accordingly, the objects of the invention include:

1. To provide a prosthesis for a wrist joint which can be assembled or disassembled as needed during the implanting procedures but which will when assembled provide strong resistance against displacing forces.

2. To provide a prosthesis, as aforesaid, which will be of sufficiently simple design as to be readily made by normal manufacturing procedures.

3. to provide a prosthesis, as aforesaid, which can be readily and easily implanted into bone structure on either side of a joint such as a wrist joint.

4. To provide a prosthesis, as aforesaid, which will be strong and sturdy in operation and enable the user to perform all normal wrist functions.

5. To provide a prosthesis, as aforesaid, which closely approximates the normal wrist joint motions.

6. To provide a prosthesis, which can be used for either right-hand or left-hand implantation without change in the relative positions of the parts thereof.

Other objects and purposes of the invention will be apparent to persons acquainted with devices of this general type upon reading the following specification and inspection of the accompanying drawings.

SUMMARY OF THE INVENTION

Figure 1:
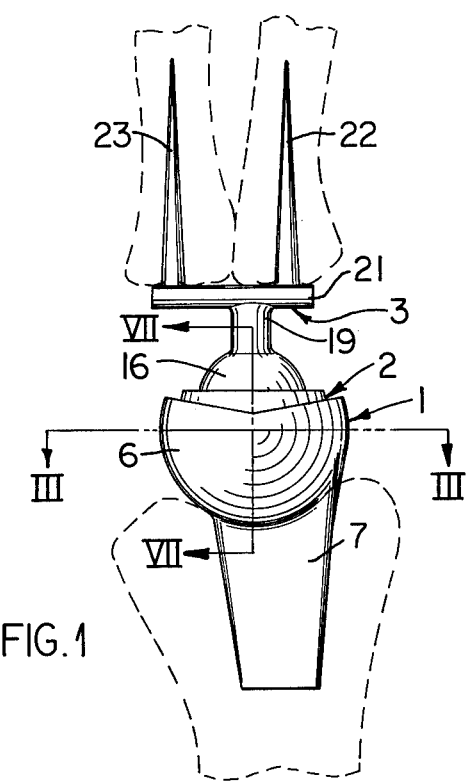
FIG. 1 shows a side view of an endoprosthetic joint embodying the invention positioned for a left-hand implantation and with the bones associated therewith indicated in phantom.

In meeting the objects and purposes above outlined, an endoprosthesis has been provided comprising first and second metallic members both made of biologically inert metal, said first adapted for insertion into an arm bone adjacent the wrist joint and said second adapted for insertion into finger bones adjacent the wrist joint. An intermediate member comprising a cup-shaped member made from plastics material which is both biologically inert and self-lubricating with respect to the aforesaid metal members is inserted between said metal members to both guide and provide a low-friction relationship therebetween. Said plastics member is so related to the first metallic member as to permit motion only in a single plane with respect thereto and the second, or finger, metallic member is so related to said plastics member as to provide relative motion therebetween only in a single plane, said two planes being at substantially right angles with respect to each other. This, therefore, provides for free universal motion between the hand and the arm and yet prevents rotation of the hand with respect to the arm about an axis comprising essentially an extension of the the central axis of the subject's forearm.

DETAILED DESCRIPTION

Referring now to the drawings in more detail, there is shown a first, or wrist, member 1, an intermediate member 2 and a second, or finger, member 3. Said wrist member and finger member are both made of any known biologically inert metal, such as Vitallium (standard formulation ASTM F-75). The intermediate member 2 is made of plastics material which is both biologically inert and possessed of reasonable self-lubricating qualities with respect to the two metallic members, such as an ultra high molecular weight polyethylene, for example, that is made by Ruhrchemie, A.G., of Oberhausen, Germany, and sold under the trademark Hostalen GUR No. 412.

Said wrist member 1 comprises a socket portion 6 from which projects a relatively heavy prong 7. Said prong is adapted for reception into a selected one of the arm bones, normally the radius bone. Said socket portion 6 is generally hemispherical externally and has an internal recess 8 which is generally hemispherical excepting that it is contoured to define an internal surface of slightly more than 180° on at least some diametric planes in order to provide the snapping action hereinafter further discussed. Said internal recess 8 has a slot 9 in the bottom thereof for purposes appearing further hereinafter.

Intermediate member 2 is of plastics material as above mentioned, is of generally hemispherical shape externally and has an internal socket 11. Said internal socket 11 is generally hemispherical but defines a surface of somewhat more than 180° on at least some diametric planes to provide the snapping relatonship with the finger portion 3 hereinafter further discussed. Said intermediate member 2 has a guide 12 projecting from its central bottom portion, same being of width to fit snugly into the slot 9 without, however, inhibiting free movement along said slot and of length to positively prevent rotation of the intermediate member 2 with respect to the socket 6. The external surface of the intermediate member 2 defines slightly more than 180°on all or most diametric planes and is of such dimension and contour that in view of the resiliency of the plastics material of which it is made it will snap into place within the recess 8 of the socket 6. Such snapping into place is of such degree that it will resist but not entirely prevent removal of the intermediate member 2 from the recess 8 but same may be snapped together reasonably easily by the surgeon during an implanting procedure.

The finger member 3 comprises a ball member 16 which is of such shape and dimension as to snap into the socket 11 of the intermediate member 2 and to resist but not prevent removal therefrom. Particularly, said ball member presents a generally spherical surface defining more than 180° of arc in at least those diametric planes where the socket 11 defines over 180°of arc. Again, as with the intermediate member 2 and its relationship to the socket 6, said ball member 16 should be readily snappable into the socket 11 during an implanting procedure but it should effect substantial resistance against removal therefrom in order to provide the wrist with the desired degree of strength. The intermediate plastic member 2 has a slot 17 in the bottom of the socket 11 thereof which is aligned perpendicularly to the slot 9 above mentioned. Said ball 16 has a guide 18 projecting from the bottom thereof which guide is of width to fit snugly but slidably into the slot 17 and is of length sufficient to positively prevent rotation of said ball 16 with respect to the intermediate plastics member 2.

Said ball 16 also has projecting from it a suitable post 19 which supports appropriate means for affixing same to one or more finger bones. In the present embodiment, post 19 supports a cross member 21 which in turn supports at its respective ends the prongs 22 and 23. Each of these prongs are receivable into an appropriate hand bone such as the second and third metacarpal bones, respectively.

With this arrangement, the prong 7 is inserted into the radius bone of the patient's arm while the prongs 22 and 23 are inserted into the second and third metacarpal bones of his hand. The ball 16, the intermediate member 2 and the socket 6, if not previously assembled, are all then appropriately snapped together with the guide 18 in the slot 17 and the guide 12 in the slot 9. This permits the movement of the hand with respect tothe arm in any direction with respect thereto but the relationship of the rectangular guides 18 and 12 with the respectively associated slots 17 and 9 positively prevents any rotation of said wrist around a projected long axis of the associated arm.

Thus, the prosthesis will provide the desired motion of the hand with respect to the arm but will prevent an undesired motion and the muscles are enabled to operate same in an entirely natural manner.

Figure 2:
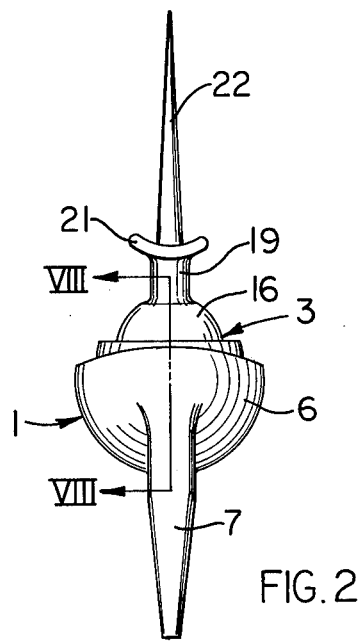
FIG. 2 shows a side view of the joint FIG. 1.
Figure 3:
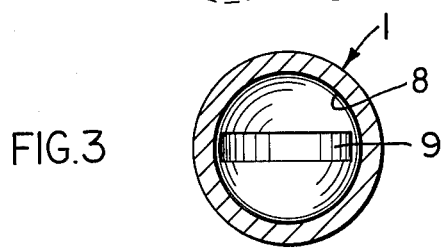
FIG. 3 is a section taken on the line III—III of FIG. 1 but with the internal components removed.
Figure 4:
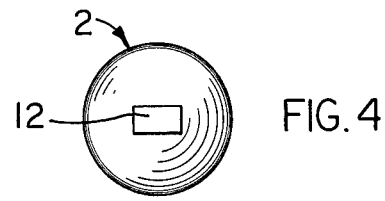
FIG. 4 is a bottom view of the plastic bearing portion of said joint.
Figure 5:
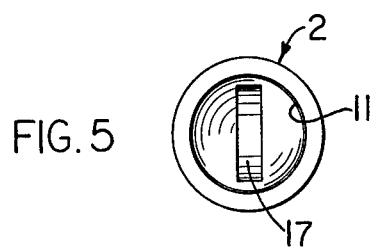
FIG. 5 is a top view of the plastic bearing portion of said joint.
Figure 6:
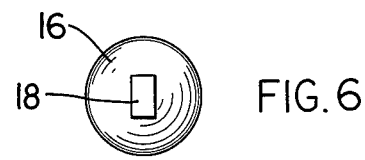
FIG. 6 is a bottom view of the finger end of said joint.
Figure 7:
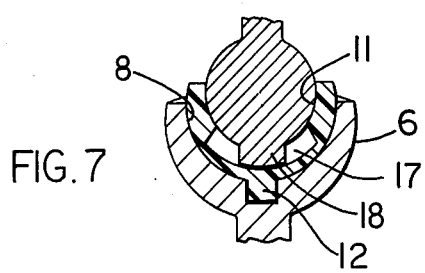
FIG. 7 is a sectional taken on the line VII—VII of FIG. 1.
Figure 8:
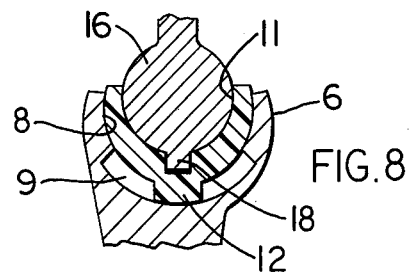
FIG. 8 is a section taken on the line VIII—VIII of FIG. 2.

It will be noted that the prong 7 is slightly offset laterally with respect to the center of the socket 6 and similarly the prongs 22 and 23 are offset somewhat from the center of the post 19. Further, upon inspection of FIG. 2 it will be noted that in the plane therein shown the parts are symmetrical about their respective central planes. Thus, the unit is made adaptable for either right-hand or left-hand installation without change in the relative positions of its parts but its overall simplicity is retained. Specifically, as shown in FIG. 1, the device is adapted for use in a left hand. When the prosthesis is to be used with the right hand, it is simply inverted right to left without other change. Thus, it is self-evident that the design hereby presented will effectively reduce inventory which would otherwise need to be carried and thereby to reduce the overall cost of this device.

Although a particular preferred embodiment of the invention has been disclosed in detail for illustrative purposes, it will be recognized that variations or modificatons of the disclosed apparatus, including the rearrangement of parts, lie within the scope of the present invention.

The embodiments of the invention in which an exclusive property or privilege is claimed are defined as follows:

1. An endoprosthetic joint for a wrist comprising:
means defining a first, or wrist, member including a socket and having also a prong projecting therefrom, an intermediate member related to the socket of said first member for pivotal motion with respect thereto in only a first plane and a second, or finger, member related to said intermediate member for pivotal motion with respect thereto in only a second plane, said first being at a substantially right angle with respect to said second plane and means associated with said finger member for connecting same to finger bones.

2. The device of claim 1 wherein said first and second members are of biologically inert metal.

3. The device of claim 1 wherein said intermediate member is of biologically inert plastics material which material is also self-lubricating with respect to the material from which said first and second members are made.

4. The device of claim 1 wherein said intermediate member presents a generally hemispherical external surface which is snappable into a similar generally hemispherical socket in said first member for providing a pivotal relationship therebetween and guide means restricting same essentially to motion in only a first plane and said second member including a ball which is snappable into a socket in said intermediate member for providing a pivotal relaionship therebetween and guide means restricting same to motion in only a secnd plane, said second plane being substantially perpendicular to said first plane.

5. The device of claim 1 wherein there are two finger prongs mounted onto a crossbar and said crossbar is in turn mounted onto said second, or finger, member.

6. The device of claim 4 wherein each of said guide means includes a rectangular projection from one of two adjacent members and an elongated rectangular slot in the other thereof snugly and slidably receiving said projection.

7. The device of claim 6 wherein said projection is on the convex surface of each pair of adjacent members and the slot is on the concave surface of the other of each said pair.

8. The device of claim 4 wherein the socket of said first member comprises a recess defining a circle of over 180° on at least some diametric planes therethrough in order to effect a smap assembly between said first member and said intermediate member.

9. The device of claim 4 wherein the socket in said intermediate member defines a circle of over 180° on at least some diametric planes therethrough to provide a snap assembly between said intermediate member and said ball of said second member.

* * * * *

UNITED STATES PATENT AND TRADEMARK OFFICE
CERTIFICATE OF CORRECTION

PATENT NO. : 4 040 130
DATED : August 9, 1977
INVENTOR(S) : George R. Laure

It is certified that error appears in the above-identified patent and that said Letters Patent are hereby corrected as shown below:

Column 4, line 27; change "said first being" to ---said first plane being---.

Column 4, line 45; change "secnd" to ---second---.

Column 4, line 63; change "smap" to ---snap---.

Signed and Sealed this

First Day of November 1977

[SEAL]

Attest:

RUTH C. MASON
Attesting Officer

LUTRELLE F. PARKER
Acting Commissioner of Patents and Trademarks